US012657960B2

(12) United States Patent
Kim

(10) Patent No.: US 12,657,960 B2
(45) Date of Patent: Jun. 16, 2026

(54) DISPLAY DEVICE AND METHOD OF DRIVING THE SAME

(71) Applicant: Samsung Display Co., LTD., Yongin-si (KR)

(72) Inventor: Chul Kim, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 172 days.

(21) Appl. No.: 18/582,477

(22) Filed: Feb. 20, 2024

(65) Prior Publication Data

US 2024/0371204 A1 Nov. 7, 2024

(30) Foreign Application Priority Data

May 2, 2023 (KR) ........................ 10-2023-0057218

(51) Int. Cl.
| | |
|---|---|
| *G06V 40/40* | (2022.01) |
| *A61B 5/024* | (2006.01) |
| *G06V 40/13* | (2022.01) |
| *G09G 3/20* | (2006.01) |
| *G09G 3/32* | (2016.01) |

(Continued)

(52) U.S. Cl.
CPC .............. *G06V 40/45* (2022.01); *A61B 5/024* (2013.01); *A61B 5/02416* (2013.01); *G06V 40/1318* (2022.01); *G09G 3/2074* (2013.01); *G09G 3/32* (2013.01); *G09G 3/3208* (2013.01); *G09G 3/3233* (2013.01); *H10K 59/60* (2023.02); *G09G 2300/0819* (2013.01); *G09G 2300/0842* (2013.01); *G09G 2300/0861* (2013.01);

(Continued)

(58) Field of Classification Search
CPC ................ A61B 5/024; A61B 5/02416; G06V 40/1318; G06V 40/45; G09G 3/2074; G09G 3/32; G09G 3/3208; G09G 3/3233; G09G 2300/0819; G09G 2300/0842; G09G 2300/0861; G09G 2354/00; G09G 2360/14; G09G 2360/142; H10K 59/60
See application file for complete search history.

(56) References Cited

U.S. PATENT DOCUMENTS

| | | | |
|---|---|---|---|
| 10,268,874 B2 | 4/2019 | Ohno et al. | |
| 2016/0180138 A1* | 6/2016 | Riedijk | .............. G01R 27/2605 |
| | | | 324/686 |

(Continued)

FOREIGN PATENT DOCUMENTS

| | | |
|---|---|---|
| JP | 3627615 B2 | 3/2005 |
| JP | 7088225 B2 | 6/2022 |

(Continued)

*Primary Examiner* — Cory A Almeida
(74) *Attorney, Agent, or Firm* — Womble Bond Dickinson (US) LLP

(57) ABSTRACT

A display device includes: a plurality of pixels in which at least a first portion of the pixels positioned in a selected area are configured to emit light in a sensing pattern; and a plurality of light sensors configured to generate sensing signals corresponding to a received light amount, wherein the selected area comprises a first area and a second area, and wherein in a first mode, a second portion of pixels positioned in the first area are configured to emit light in the sensing pattern, and to generate first sensing information using sensing signals generated by light sensors positioned in the second area, which does not overlap the first area.

18 Claims, 14 Drawing Sheets

(51) Int. Cl.
    *G09G 3/3208*     (2016.01)
    *G09G 3/3233*     (2016.01)
    *H10K 59/60*     (2023.01)

(52) U.S. Cl.
    CPC ..... *G09G 2354/00* (2013.01); *G09G 2360/14*
        (2013.01); *G09G 2360/142* (2013.01)

(56)         References Cited

U.S. PATENT DOCUMENTS

| | | | |
|---|---|---|---|
| 2019/0065717 A1* | 2/2019 | Won | G06V 40/1365 |
| 2021/0073507 A1 | 3/2021 | Kim et al. | |

FOREIGN PATENT DOCUMENTS

| | | |
|---|---|---|
| KR | 10-1798395 B1 | 11/2017 |
| KR | 10-1923335 B1 | 2/2019 |
| KR | 10-2021-0029891 A | 3/2021 |
| WO | WO 2017/076292 A1 | 5/2017 |

* cited by examiner

DISPLAY DEVICE AND METHOD OF DRIVING THE SAME

CROSS REFERENCE TO RELATED APPLICATION

The present application claims priority to and the benefit of Korean Patent Application No. 10-2023-0057218, filed on May 2, 2023, in the Korean Intellectual Property Office, the entire disclosure of which is incorporated herein by reference.

BACKGROUND

1. Field

Aspects of some embodiments of the present disclosure relate to a display device and a method of driving the same.

2. Description of the Related Art

As information technology develops, the importance of display devices, which provide a connection medium between users and information, has been highlighted. In response to this, a use of a display device such as a liquid crystal display device and an organic light emitting display device is increasing.

Display devices may be capable of sensing a user's fingerprint using a plurality of light sensors and performing a user authentication function. However, when fingerprint sensing is performed by using light, it may be difficult to distinguish a forged fingerprint (or a fake fingerprint) from a valid fingerprint, and thus a security problem may occur.

The above information disclosed in this Background section is only for enhancement of understanding of the background and therefore the information discussed in this Background section does not necessarily constitute prior art.

SUMMARY

Aspects of some embodiments of the present disclosure include a display device and a method of driving the same that may be capable of sensing a fingerprint using light and discriminating between a forged fingerprint and a valid fingerprint with relatively minimal configuration.

According to some embodiments of the present disclosure, a display device includes a plurality of pixels in which at least a portion of the pixels positioned in a selected area emits light in a sensing pattern, a plurality of light sensors configured to generate sensing signals corresponding to a received light amount, and a readout circuit generates sensing information based on the sensing signals, wherein the selected area comprises a first area and a second area, and wherein in a first mode, a portion of pixels positioned in the first area emits light in the sensing pattern, and the readout circuit generates first sensing information using sensing signals generated by light sensors positioned in the second area, which does not overlap the first area.

According to some embodiments, pixels positioned in the second area may be in a non-emission state.

According to some embodiments, an outer side of the first area may be completely surrounded by the second area.

According to some embodiments, in a second mode, a portion of the pixels positioned in the first area and a portion of pixels positioned in the second area may emit light in the sensing pattern, and the readout circuit generates second sensing information using sensing signals generated by light sensors positioned in the first area and the second area.

According to some embodiments, a generation cycle of the first sensing information may be shorter than a generation cycle of the second sensing information.

According to some embodiments, the first sensing information may be photoplethysmography (PPG) information, and the second sensing information may be fingerprint image information.

According to some embodiments, whether the second sensing information is valid may be determined using the first sensing information.

According to some embodiments, the readout circuit may include a readout unit connected to a portion of the light sensors through a readout line, and the readout unit may include an amplifier connected to the portion of the light sensors through the readout line, a first capacitor connected between a first input terminal and an output terminal of the amplifier, a first switch connected with the first capacitor in parallel, a second capacitor, a second switch connecting the second capacitor and the output terminal, a third capacitor, and a third switch connecting the third capacitor and the output terminal.

According to some embodiments, in a state in which the first switch is turned off, the second switch and the third switch may be sequentially turned on.

According to some embodiments, a turn-on period of the second switch and a turn-on period of the third switch may not overlap.

According to some embodiments, a turn-on period of the third switch in the first mode may be longer than the turn-on period of the third switch in the second mode.

According to some embodiments, a turn-off period of the first switch in the first mode may be longer than a turn-off period of the first switch in the second mode.

According to some embodiments, a turn-on period of the second switch in the first mode may have the same length as a turn-on period of the second switch in the second mode.

According to some embodiments of the present disclosure, a method of driving a display device includes selecting a partial area of a plurality of pixels, emitting light in a sensing pattern by at least a portion of pixels positioned in a selected area, generating, by a plurality of light sensors, sensing signals corresponding to a received light amount, and generating, by a readout circuit, sensing information based on the sensing signals, wherein the selected area comprises a first area and a second area, and wherein in a first mode, a portion of pixels positioned in the first area emits light in the sensing pattern, and the readout circuit generates first sensing information using sensing signals generated by light sensors positioned in the second area, which does not overlap the first area.

According to some embodiments, pixels positioned in the second area may be in a non-emission state.

According to some embodiments, an outer side of the first area may be completely surrounded by the second area.

According to some embodiments, in a second mode, a portion of the pixels positioned in the first area and a portion of pixels positioned in the second area may emit light in the sensing pattern, and the readout circuit generates second sensing information using sensing signals generated by light sensors positioned in the first area and the second area.

According to some embodiments, a generation cycle of the first sensing information may be shorter than a generation cycle of the second sensing information.

According to some embodiments, the first sensing information may be photoplethysmography (PPG) information, and the second sensing information may be fingerprint image information.

According to some embodiments, whether the second sensing information is valid may be determined using the first sensing information.

According to some embodiments, the display device and the method of driving the same may sense a fingerprint using light and discriminate a forged fingerprint with a minimum configuration.

BRIEF DESCRIPTION OF THE DRAWINGS

The above and other features and characteristics of embodiments according to the present disclosure will become more apparent by describing in further detail aspects of some embodiments thereof with reference to the accompanying drawings, in which.

DETAILED DESCRIPTION

Figure 1:
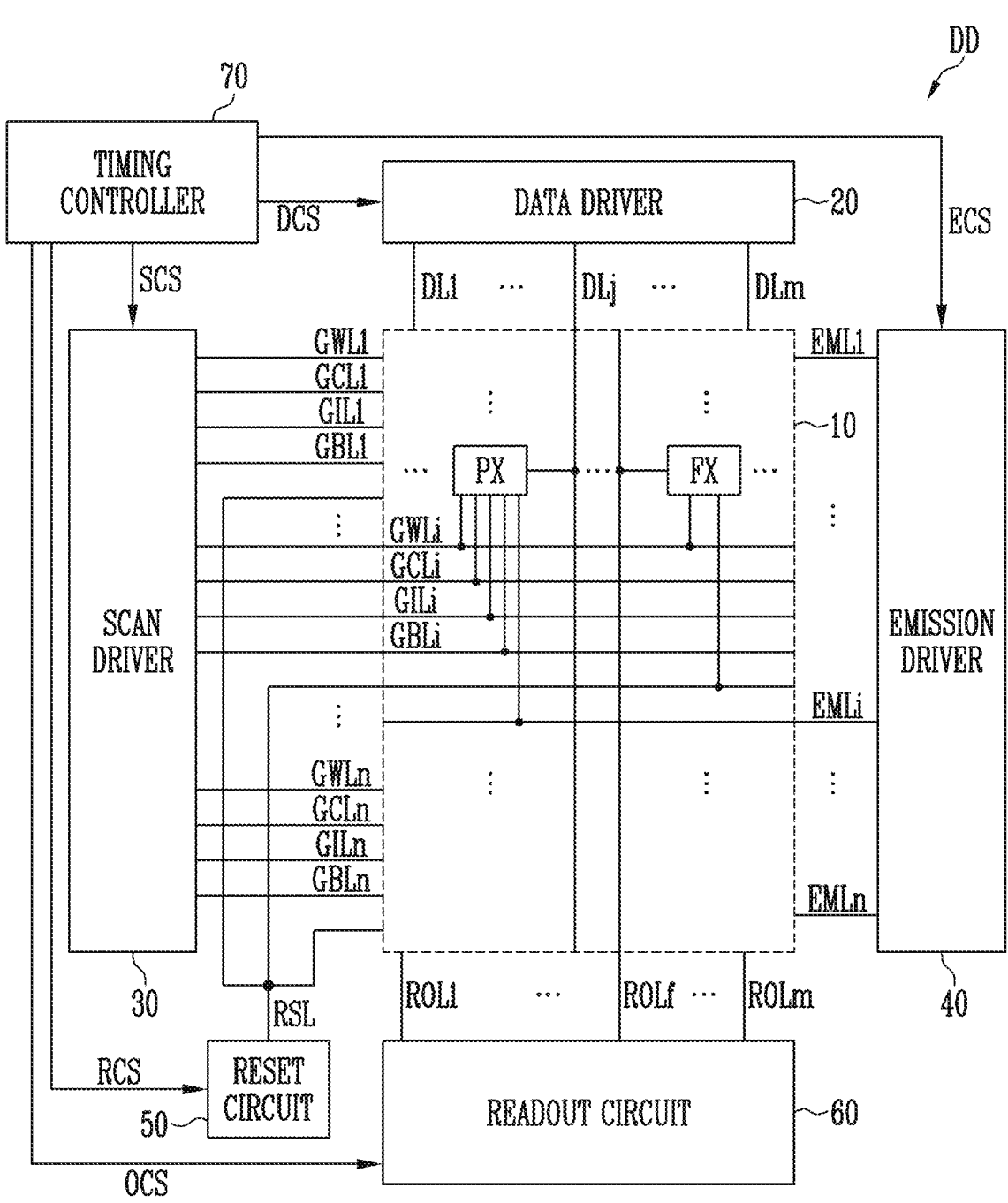
FIG. 1 is a diagram illustrating a display device according to some embodiments of the present disclosure.

Hereinafter, aspects of some embodiments of the present disclosure will be described in more detail with reference to the accompanying drawings so that those skilled in the art may carry out embodiments according to some embodiments of the present disclosure. Embodiments according to the present disclosure may be implemented in various different forms and is not limited to the embodiments described herein.

In order to more clearly describe embodiments according to the present disclosure, parts that are not related to, or necessary for understanding, the description may be omitted for brevity, and the same or similar elements are denoted by the same reference numerals throughout the specification. Therefore, the above-described reference numerals may be used in other drawings.

In addition, sizes and thicknesses of each component shown in the drawings are arbitrarily shown for convenience of description, and thus embodiments according to the present disclosure are not necessarily limited to those shown in the drawings. In the drawings, thicknesses may be exaggerated to clearly express various layers and areas.

In addition, an expression "is the same" in the description may mean "is substantially the same". That is, the expression "is the same" may be the same enough for those of ordinary skill to understand that it is the same. Other expressions may also be expressions in which "substantially" is omitted.

FIG. 1 is a diagram illustrating a display device according to some embodiments of the present disclosure.

Referring to FIG. 1, a display device according to some embodiments of the present disclosure may include a display panel 10, a data driver 20, a scan driver 30, an emission driver 40, a reset circuit 50, a readout circuit 60, and a timing controller 70.

The timing controller 70 may receive grayscales and timing signals for each frame period from a processor. Here, the processor may correspond to at least one of a graphics processing unit (GPU), a central processing unit (CPU), an application processor (AP), and/or the like. The timing signals may include a vertical synchronization signal, a horizontal synchronization signal, a data enable signal, and the like.

Each cycle of the vertical synchronization signal may correspond to each frame period. Each cycle of the horizontal synchronization signal may correspond to each horizontal period. The grayscales may be supplied in a horizontal line unit in each horizontal period in response to a pulse of an enable level of the data enable signal. A horizontal line may refer to pixels (for example, a pixel row) connected to the same scan line and emission line.

The timing controller 70 may generate a first control signal SCS, a second control signal ECS, a third control signal DCS, a fourth control signal RCS, and a fifth control signal OCS based on the received grayscales and timing signals. The first control signal SCS may be supplied to the scan driver 30, the second control signal ECS may be supplied to the emission driver 40, the third control signal DCS may be supplied to the data driver 20, the fourth control signal RCS may be supplied to the reset circuit 50, and the fifth control signal OCS may be supplied to the readout circuit 60. The timing controller 70 may rearrange (for example, render) and correct the grayscales, and supply the grayscales to the data driver 20.

The display panel 10 may include pixels PX connected to data lines DL1, . . . , DLj, . . . , and DLm, scan lines GWL1, . . . , GWLi, . . . , GWLn, GCL1, . . . , GCLi, . . . , GCLn, GIL1, . . . , GILi, . . . , GILn, GBL1, . . . , GBLi, . . . , and GBLn, and emission lines EML1, . . . , EMLi, . . . , and EMLn. In addition, the display panel 10 may include light sensors FX connected to first scan lines GWL1, . . . , GWLi, . . . , and GWLn, a reset line RSL, and readout lines ROL1, . . . , ROLf, . . . , and ROLm. Here, m and n may be integers greater than 1. The pixels PX may include light emitting elements, and the light sensors FX may include light receiving elements.

The data driver 20 may receive the grayscales and the third control signal DCS from the timing controller 70. For example, the third control signal DCS may include a source start signal, a clock signal, and the like. For example, the data driver 20 may sample the grayscales while shifting the source start signal based on the clock signal, and apply data voltages corresponding to the sampled grayscales to the data lines DL1 to DLm in a pixel row unit.

The scan driver 30 may receive the first control signal SCS from the timing controller 70. The first control signal SCS may include a clock signal, a scan start signal, and the like. The scan driver 30 may supply scan signals to the scan lines GWL1, . . . , GWLi, . . . , GWLn, GCL1, . . . , GCLi, . . . , GCLn, GIL1, . . . , GILi, . . . , GILn, GBL1, . . . , GBLi, . . . , GBLn in response to the first control signal SCS.

FIG. 1 illustrates embodiments provided as a configuration in which the scan lines GWL1, . . . , GWLi, . . . , GWLn, GCL1, . . . , GCLi, . . . , GCLn, GIL1, . . . , GILi, . . . , GILn, GBL1, . . . , GBLi, . . . , and GBLn are connected to one scan driver 30 is shown, but is not limited thereto. For example, the scan driver 30 may include a first sub-scan driver connected to the first scan lines GWL1, . . . , GWLi, . . . , and GWLn, a second sub-scan driver connected to second scan lines GCL1, . . . , GCLi, . . . , and GCLn, a third sub-scan driver connected to third scan lines GIL1, . . . , GILi, . . . , and GILn, and a fourth sub-scan driver connected to fourth scan lines GBL1, . . . , GBLi, . . . , and GBLn. In another example, the scan driver 30 may be configured to include a first sub-scan driver connected to the scan lines GWL1, . . . , GWLi, . . . , GWLn, GBL1, . . . , GBLi, . . . , and GBLn a second sub-scan driver connected to the scan lines GCL1, . . . , GCLi, . . . , GCLn, GIL1, . . . , GILi, . . . , and GILn.

The scan driver 30 or each sub-scan driver may sequentially supply scan signals having a pulse of a turn-on level to corresponding scan lines. The scan driver 30 or each sub-scan driver may include scan stages configured in a form of a shift register. The scan driver 30 or each sub-scan driver may generate the scan signals in a method of sequentially transferring the scan start signal that is a pulse form of a turn-on level to a next scan stage according to control of the clock signal.

The emission driver 40 may receive the second control signal ECS from the timing controller 70. The second control signal ECS may include a clock signal, an emission stop signal, and the like. The emission driver 40 may supply emission signals to the emission lines EML1 to EMLn in response to the second control signal ECS.

The emission driver 40 may sequentially supply emission signals having a pulse of a turn-off level to the emission lines EML1 to EMLn. The emission driver 40 may include emission stages configured in a form of a shift register. The emission driver 40 may generate the emission signals in a method of sequentially transferring the emission stop signal that is a pulse form of a turn-off level to a next emission stage according to control of the clock signal.

FIG. 1 illustrates embodiments in which the scan driver 30 and the emission driver 40 are provided as separate configurations is shown, but embodiments according to the present disclosure are not limited thereto. For example, the scan driver 30 and the emission driver 40 may be integrated into one driving circuit, one module, or the like.

The reset circuit 50 may receive the fourth control signal RCS from the timing controller 70. The reset circuit 50 may apply a reset signal to a reset line RSL in response to the fourth control signal RCS. The reset line RSL may be commonly connected to all light sensors FX of the display panel 10. That is, a common reset signal may be transferred to all light sensors FX. Meanwhile, according to some embodiments, the reset circuit 50 may be connected to a plurality of light sensors FX through a plurality of reset lines. In this case, a plurality of different reset signals may be transferred to different light sensors FX.

For sensing, at least a portion of pixels PX positioned in a selected area may emit light in a sensing pattern. The sensing pattern may be a single color pattern (for example, a red pattern or a green pattern). Meanwhile, the light sensors FX may generate sensing signals corresponding to received light amount. Pixels PX positioned outside the selected area may continue to display an existing image. Because a user may not recognize the sensing pattern of the pixels PX positioned in the selected area covered by a finger, the user may continue to enjoy the existing image.

The readout circuit 60 may receive the fifth control signal OCS from the timing controller 70. The readout circuit 60 may provide sensing information based on sensing signals received from readout lines ROL1 to ROLm in response to the fifth control signal OCS. The sensing information may be variously configured according to a mode of the display device DD. For example, in a first mode, first sensing information may be photoplethysmography (PPG) information. Meanwhile, in a second mode, second sensing information may be fingerprint image information.

The processor or the timing controller 70 may perform a user authentication function or the like using the sensing information provided from the readout circuit 60.

Figure 2:
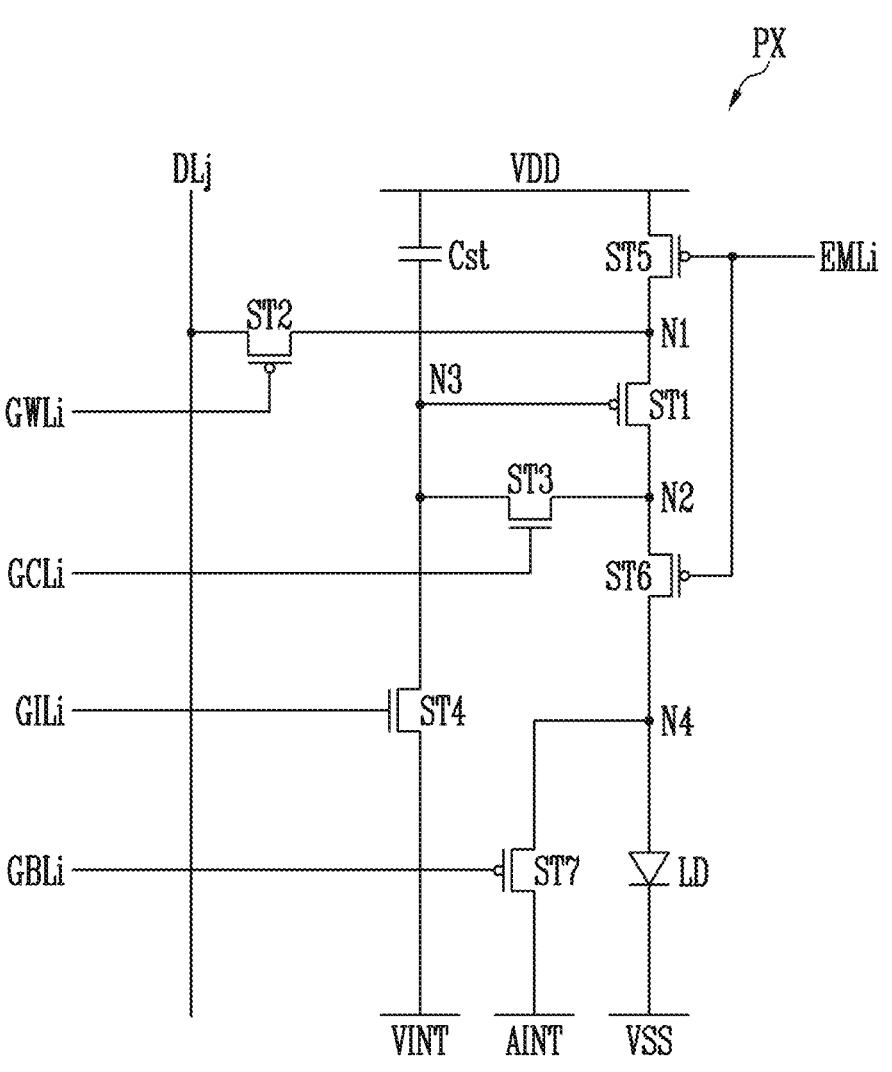
FIG. 2 is a diagram illustrating a pixel according to some embodiments of the present disclosure.

FIG. 2 is a diagram illustrating a pixel according to some embodiments of the present disclosure.

In FIG. 2, a pixel PX located in an i-th pixel row and a j-th pixel column among the plurality of pixels PX is shown as an example. A pixel row may indicate pixels connected to the same scan lines and emission line, and a pixel column may indicate pixels connected to the same data line. Here, i is an integer greater than or equal to 1 and less than or equal to n, and j is an integer greater than or equal to 1 and less than or equal to m.

Referring to FIG. 2, the pixel PX may include pixel transistors ST1 to ST7, a light emitting element LD, and a storage capacitor Cst, but embodiments according to the present disclosure are not limited thereto.

A first electrode of the first pixel transistor ST1 (driving transistor) may be connected to a first node N1, a second electrode may be connected to a second node N2, and a gate electrode may be connected to a third node N3. The first pixel transistor ST1 may control a driving current flowing from a first power voltage VDD to a second power voltage VSS via the light emitting element LD in response to a voltage of the third node N3.

A first electrode of the second pixel transistor ST2 (switching transistor) may be connected to a data line DLj, a second electrode may be connected to the first node N1, and a gate electrode may be connected to the first scan line GWLi. The second pixel transistor ST2 may be turned on when a first scan signal of a turn-on level is supplied to the first scan line GWLi, to electrically connect the data line DLj and the first electrode of the first pixel transistor ST1.

A first electrode of the third pixel transistor (diode connection transistor ST3) may be connected to the second node N2, a second electrode may be connected to the third node N3, and a gate electrode may be connected to the second scan line GCLi. The third pixel transistor ST3 may be turned on when a second scan signal of a turn-on level is supplied to the second scan line GCLi, to electrically connect the second electrode and the gate electrode of the first pixel transistor ST1. That is, when the third pixel transistor ST3 is turned on, the first pixel transistor ST1 may be connected in a diode configuration.

A first electrode of the fourth pixel transistor ST4 (gate initialization transistor) may be connected to the third node N3, a second electrode may be connected to a first initialization voltage line to which a first initialization voltage VINT is applied, and a gate electrode may be connected to the third scan line GILi. The fourth pixel transistor ST4 may be turned on when a third scan signal GI[i] of a turn-on level is supplied to the third scan line GILi, to supply the first initialization voltage VINT to the third node N3.

A first electrode of the fifth pixel transistor ST5 (first light emitting transistor) may be connected to a first power line to which the first power voltage VDD is applied, a second electrode may be connected to the first node N1, and a gate electrode may be connected to the emission line EMLi. The fifth pixel transistor ST5 may be turned off when an emission signal of a turn-off level is supplied to the emission line EMLi, and may be turned on in other cases.

A first electrode of the sixth pixel transistor ST6 (second light emitting transistor) may be connected to the second node N2, a second electrode may be connected to a fourth node N4, and a gate electrode may be connected to the emission line EMLi. The sixth pixel transistor ST6 may be turned off when an emission signal of a turn-off level is supplied to the emission line EMLi, and may be turned on in other cases.

A first electrode of the seventh pixel transistor ST7 (anode initialization transistor) may be connected to the fourth node N4, a second electrode may be connected to a second initialization voltage line to which a second initialization voltage AINT is applied, and a gate electrode may be connected to the fourth scan line GBLi. The seventh pixel transistor ST7 may be turned on when a fourth scan signal of a turn-on level is supplied to the fourth scan line GBLi, to supply the second initialization voltage AINT to the fourth node N4.

Among the pixel transistors ST1 to ST7, each of some ST1, ST2, ST5, ST6, and ST7 of the transistors may be a P-type transistor, and each of the other transistors ST3 and ST4 may be an N-type transistor. However, embodiments according to the present disclosure are not limited thereto. For example, each of the pixel transistors ST1 to ST7 may be a P-type transistor or an N-type transistor.

A first electrode of the storage capacitor Cst may be connected to the first power line to which the first power voltage VDD is applied, and a second electrode may be connected to the third node N3.

An anode of the light emitting element LD may be connected to the fourth node N4 and a cathode may be connected to a second power line to which the second power voltage VSS is applied. The light emitting element LD may be a light emitting diode. The light emitting element LD may be configured of an organic light emitting element (organic light emitting diode), an inorganic light emitting element (inorganic light emitting diode), a quantum dot/well light emitting element (quantum dot/well light emitting diode), or the like. The light emitting element LD may emit light in any one of a first color, a second color, and a third color. In addition, although only one light emitting element LD is provided in each pixel according to some embodiments, a plurality of light emitting elements may be provided in each pixel according to some embodiments of the present disclosure. At this time, the plurality of light emitting elements may be connected in series, parallel, series-parallel, or the like.

A pixel PX according to the present disclosure is not limited to the structure illustrated in FIG. 2. For example, according to some embodiments, the pixel PX may include additional components or fewer components without departing from the spirit and scope of embodiments according to the present disclosure.

Figure 3:
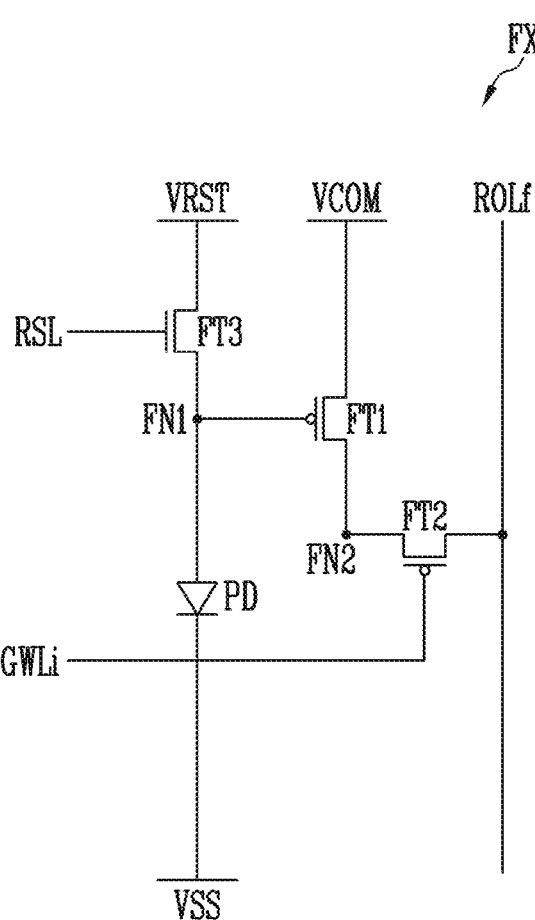
FIG. 3 is a diagram illustrating a light sensor according to some embodiments of the present disclosure.

FIG. 3 is a diagram illustrating a light sensor according to some embodiments of the present disclosure.

Referring to FIG. 3, the light sensor FX may include sensing transistors FT1 to FT3 and a light receiving element PD, but embodiments according to the present disclosure are not limited thereto.

A first electrode of a first sensing transistor FT1 (amplification transistor) may be connected to a common voltage line to which a common voltage VCOM is applied, a second electrode may be connected to a second node FN2, and a gate electrode may be connected to a first node FN1. The first sensing transistor FT1 may control a sensing current flowing through the first sensing transistor FT1 in response to a voltage of the first node FN1. The sensing current may be supplied as a sensing signal to the readout line ROLf via the second sensing transistor FT2.

A first electrode of the second sensing transistor FT2 (output transistor) may be connected to the second node FN2, a second electrode may be connected to the readout line ROLf, and a gate electrode may be connected to the first scan line GWLi. That is, the same scan line, that is, the first scan line GWLi, may be connected to the gate electrode of the second sensing transistor FT2 and the gate electrode of the second pixel transistor ST2. The second sensing transistor FT2 may be turned on when the first scan signal of the turn-on level is supplied to the first scan line GWLi, to electrically connect the second electrode of the first sensing transistor FT1 and the readout line ROLf.

A first electrode of the third sensing transistor FT3 (reset transistor) may be connected to a reset voltage line to which a reset voltage VRST is applied, a second electrode may be connected to the first node FN1, and a gate electrode may be connected to the reset line RSL. The third sensing transistor FT3 may be turned on when a reset signal of a turn-on level is supplied to the reset line RSL to supply the reset voltage VRST to the first node FN1. The first node FN1, that is, the gate electrode of the first sensing transistor FT1 may be reset by the reset voltage VRST. The reset voltage VRST may be set less than the second power voltage VSS.

Each of some FT1 and FT2 of the sensing transistors FT1 to FT3 may be a P-type transistor, and the other transistor FT3 may be an N-type transistor, but embodiments according to the present disclosure are not limited thereto. For example, each of the sensing transistors FT1 to FT3 may be a P-type transistor or an N-type transistor.

A first electrode (or an anode) of the light receiving element PD may be connected to the first node FN1, and a second electrode (or a cathode) may be connected to the second power line to which the second power voltage VSS is applied. The light receiving element PD may be a photo diode. However, according to some embodiments of the present disclosure, the light receiving element PD may be configured of a photo transistor.

When the light receiving element PD receives light, an electron may be excited, and a reverse current may flow from the cathode to the anode. Therefore, when the light receiving element PD is exposed to light, the voltage of the first node FN1 may gradually increase after a reset time point. As a light receiving time increases or an intensity of light increases, an increase amount of the voltage of the first node FN1 after the reset time point may increase. Therefore, a magnitude of the sensing current flowing through the readout line ROLf may vary according to the light receiving time and the intensity of light.

Figure 4:
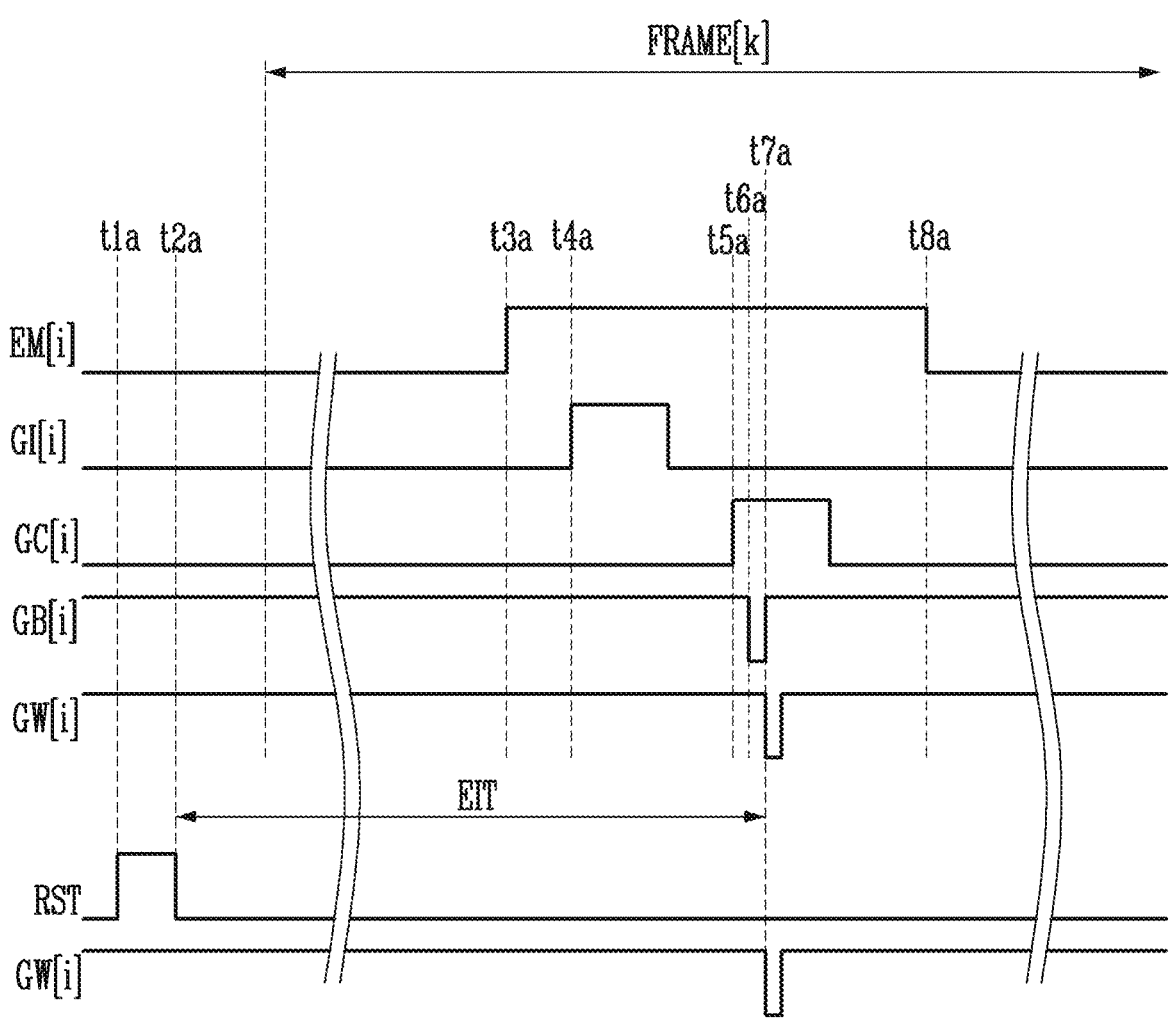
FIG. 4 is a diagram illustrating a method of driving a pixel and a light sensor according to some embodiments of the present disclosure.

FIG. 4 is a diagram illustrating a method of driving a pixel and a light sensor according to some embodiments of the present disclosure.

In FIG. 4, a process in which the pixel PX of FIG. 2 and the light sensor FX of FIG. 3 operate in an arbitrary k-th frame period FRAME[k] is described.

First, during a period t1$a$ to t2$a$ before the k-th frame period FRAME[k], the reset signal RST of the turn-on level may be applied to the reset line RSL. Therefore, the first node FN1 of the light sensor FX may be reset by the reset voltage VRST. After a time point t2$a$, the voltage of the first node FN1 gradually increases according to a length of a light receiving period EIT and a light intensity.

At a time point t3$a$, an emission signal EM[i] of a turn-off level is supplied to the emission line EMLi. Accordingly, the fifth pixel transistor ST5 and the sixth pixel transistor ST6 are turned off, and light emission of the light emitting element LD is prevented.

At a time point t4$a$, a third scan signal GI[i] of a turn-on level is supplied to the third scan line GILi. Accordingly, the fourth pixel transistor ST4 is turned on, and the third node N3 is initialized to the first initialization voltage VINT.

At a time point t5$a$, a second scan signal GC[i] of a turn-on level is supplied to the second scan line GCLi. Accordingly, the third pixel transistor ST3 is turned on and the first pixel transistor ST1 is in a diode connection state.

At a time point t6$a$, a fourth scan signal GB[i] of a turn-on level is supplied to the fourth scan line GBLi. Accordingly, the seventh pixel transistor ST7 is turned on, and the fourth node N4 is initialized to the second initialization voltage AINT. The second initialization voltage AINT may be set to a voltage equal to or lower than the second power voltage VSS, and thus the light emitting element LD may desirably express a low grayscale.

At a time point t7$a$, a first scan signal GW[i] of a turn-on level is supplied to the first scan line GWLi. Accordingly, the second pixel transistor ST2 is turned on, and the data voltage is applied to the first node N1. At this time, the third node N3 is in a state in which the first initialization voltage VINT is applied, and the first initialization voltage VINT may be a voltage sufficiently lower than the data voltages. Therefore, the first pixel transistor ST1 may be turned on, and a correction data voltage in which a threshold voltage decrease is reflected in the data voltage may be applied to the third node N3. The storage capacitor Cst maintains a voltage corresponding to a difference between the first power voltage VDD and a compensation data voltage. This period may be referred to as a threshold voltage compensation period or a data writing period.

In addition, at the time point t7$a$, the second sensing transistor FT2 is turned on by the first scan signal GW[i] of the turn-on level. Therefore, a sensing current corresponding to the light receiving period EIT and the light intensity may flow through the readout line ROLf.

At a time point t8$a$, an emission signal EM[i] of a turn-on level is supplied to the emission line EMLi. Accordingly, the fifth pixel transistor ST5 and the sixth pixel transistor ST6 are turned on, and the light emitting element LD is in a state capable of emitting light.

At this time, a driving current path connecting the first power line, the fifth pixel transistor ST5, the first pixel transistor ST1, the sixth pixel transistor ST6, the light emitting element LD, and the second power line is formed. A driving current amount flowing through the first electrode and the second electrode of the first pixel transistor ST1 is adjusted according to a voltage maintained in the storage capacitor Cst. The light emitting element LD emits light with a luminance corresponding to the driving current amount. The light emitting element LD may emit light until an emission signal EM[i] of a turn-off level is applied to the emission line EMLi.

Figure 5:
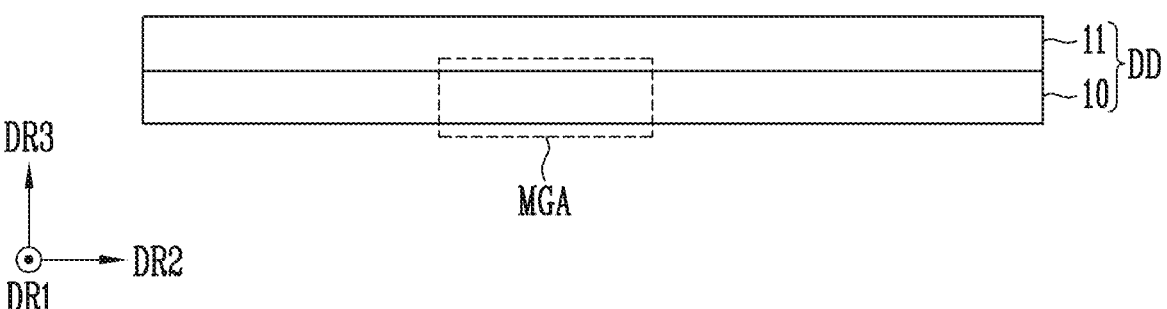
FIG. 5 is a diagram illustrating a stack relationship between a display panel and a touch sensor according to some embodiments of the present disclosure.

FIG. 5 is a diagram illustrating a stack relationship between a display panel and a touch sensor.

Referring to FIG. 5, the display device DD may include a display panel 10 and a touch sensor 11. The display panel 10 may be a flat-type display panel extending in a first direction DR1 and a second direction DR2. The first direction DR1 and the second direction DR2 may be perpendicular to each other. Similarly, the touch sensor 11 may be a flat-type touch sensor extending in the first direction DR1 and the second direction DR2.

The touch sensor 11 may be positioned in a third direction DR3 of the display panel 10. The third direction DR3 may be perpendicular to the first direction DR1 and the second direction DR2. The third direction DR3 may be an image display direction of the display panel 10. A user may intuitively control the display device DD by touching the touch sensor 11 while looking at the image in the third direction DR3 of the display panel 10. The touch sensor 11 may be implemented as an existing touch sensor such as a touch sensor of a mutual-capacitance method and a touch sensor of a self-capacitance method. According to some embodiments, the display panel 10 and the touch sensor 11 may be integrally manufactured.

Figure 6:
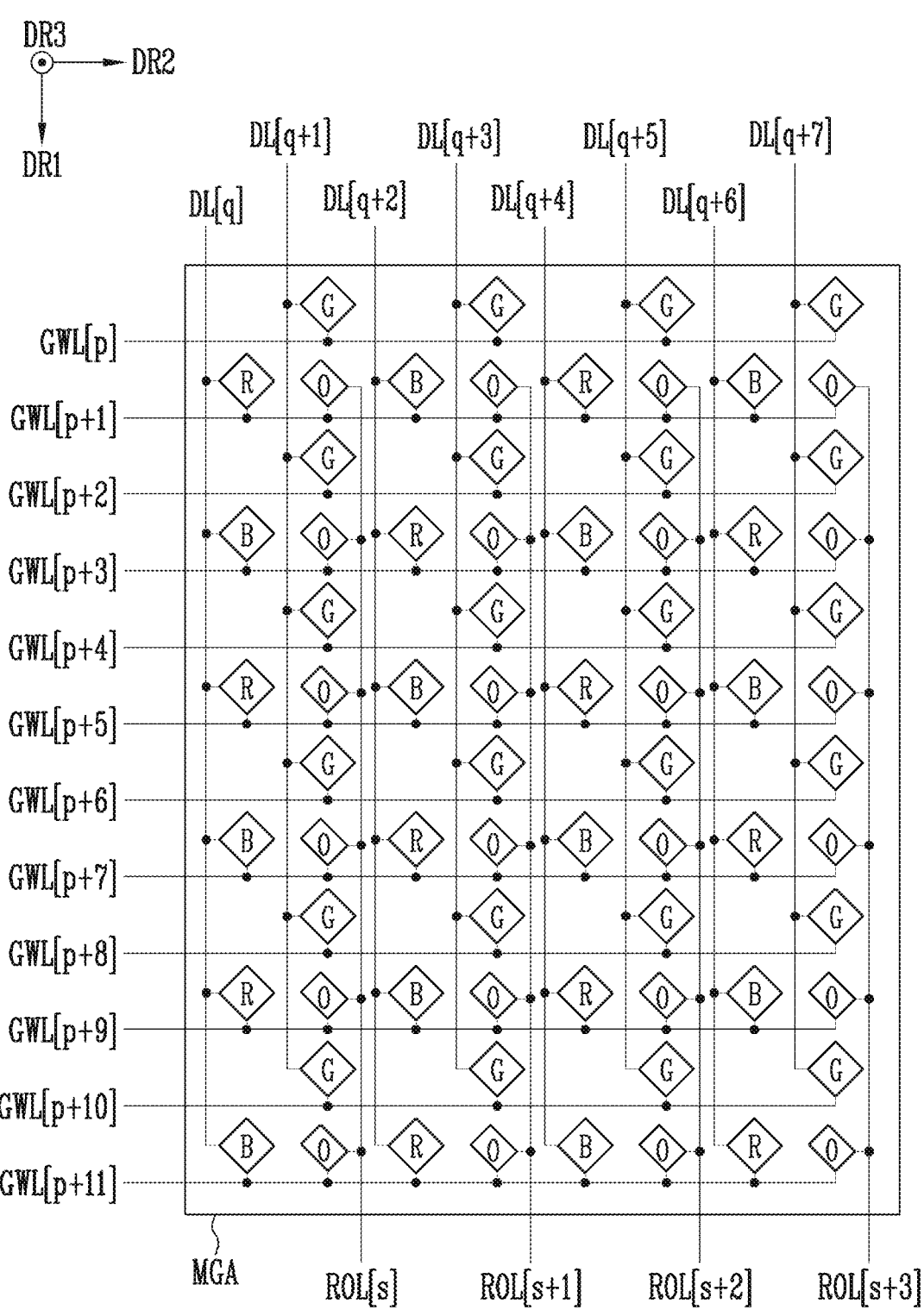
FIG. 6 is an enlarged view of a portion of a display panel 10 of FIG. 5 according to some embodiments of the present disclosure.

FIG. 6 is an enlarged view of a portion MGA of the display panel 10 of FIG. 5.

The pixels PX may be connected to first scan lines GWL[p] to GWL[p+11] and may include light emitting elements R, G, and B. The first scan lines GWL[p] to GWL[p+11] may be arranged parallel to each other in the first direction DR1. The first scan lines GWL[p] to GWL[p+11] may extend in the second direction DR2. p may be an integer greater than 0. In addition, the pixels PX may be connected to data lines DL[q] to DL[q+7]. The data lines DL[q] to DL[q+7] may extend in the first direction DR1 and may be arranged parallel to each other in the second direction DR2. q may be an integer greater than 0.

Each of the light emitting elements R, G, and B of the pixels PX may emit one of light of a first color, light of a second color, and light of a third color. The first color, the second color, and the third color may be different colors. For example, the first color may be one of red, green, and blue, the second color may be one other than the first color among red, green, and blue, and the third color may be one other than the first color and the second color among red, green, and blue. In addition, magenta, cyan, and yellow may be used instead of red, green, and blue as the first to third colors.

According to some embodiments, a connection relationship of the first scan lines GWL[p] to GWL[p+11], the data lines DL[q] to DL[q+7], and the pixels PX is shown under an assumption that the light emitting elements R, G, and B of the pixels PX are arranged in a PENTILE™ structure. For example, pixels PX including the light emitting elements R and B of the first color and the third color may be connected to the same data line DL[q], DL[q+2], DL[q+4], or DL[q+6] together, and pixels PX including the light emitting elements G of the second color may be connected to an independent data line DL[q+1], DL[q+3], DL[q+5], or DL[q+7]. The data lines DL[q], DL[q+2], DL[q+4], or DL[q+6] to which pixels PX including the light emitting elements R and B of the first color and the third color are connected and the data lines DL[q+1], DL[q+3], DL[q+5], or DL[q+7] to which the pixels PX including the light emitting elements G of the second color are connected may be alternately arranged.

In addition, the pixels PX including the light emitting elements R and B of the first color and the third color may be connected to the same first scan line GWL[p+1], GWL [p+3], GWL[p+5], GWL[p+7], GWL[p+9], or GWL[p+11] together, and the pixels PX including the light emitting elements G of the second color may be connected to an independent first scan line GWL[p], GWL[p+2], GWL[p+4], GWL[p+6], GWL[p+8], or GWL[p+10]. The first scan line GWL[p+1], GWL[p+3], GWL[p+5], GWL[p+7], GWL [p+9], or GWL[p+11] to which the pixels PX including the light emitting elements R and B of the first color and the third color and the first scan line GWL[p], GWL[p+2], GWL[p+4], GWL[p+6], GWL[p+8], or GWL[p+10] to which the pixels PX including the light emitting elements G of the second color are connected may be alternately arranged.

According to some embodiments, the light emitting elements R, G, and B of the pixels PX may be arranged in another structure such as an RGB stripe structure.

The light sensors FX including the light receiving elements O may be connected to the first scan lines GWL[p+1], GWL[p+3], GWL[p+5], GWL[p+7], GWL[p+9], or GWL [p+11]. For example, the light sensors FX including the light receiving elements O, the pixels PX including the light emitting elements R of the first color, and the pixels PX including the light emitting elements B of the third color may be connected to the same first scan lines GWL[p+1], GWL[p+3], GWL[p+5], GWL[p+7], GWL[p+9], or GWL [p+11].

The light sensors FX may be connected to a common reset line RSL (refer to FIG. 1). The light sensors FX may be connected to corresponding readout lines ROL[s] to ROL [s+3]. The readout lines ROL[s] to ROL[s+3] may extend in the first direction DR1 and may be arranged parallel to each other in the second direction DR2.

Figure 7:
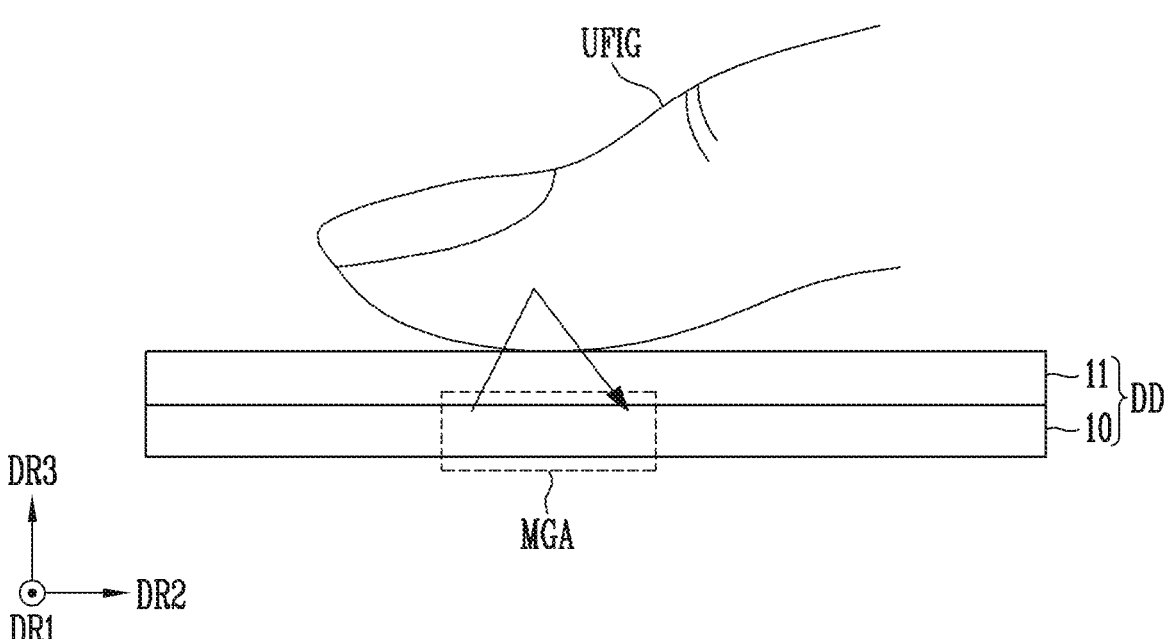
FIGS. 7 and 8 are diagrams illustrating a display device operating in a first mode with respect to a selected area according to some embodiments of the present disclosure.
Figure 8:
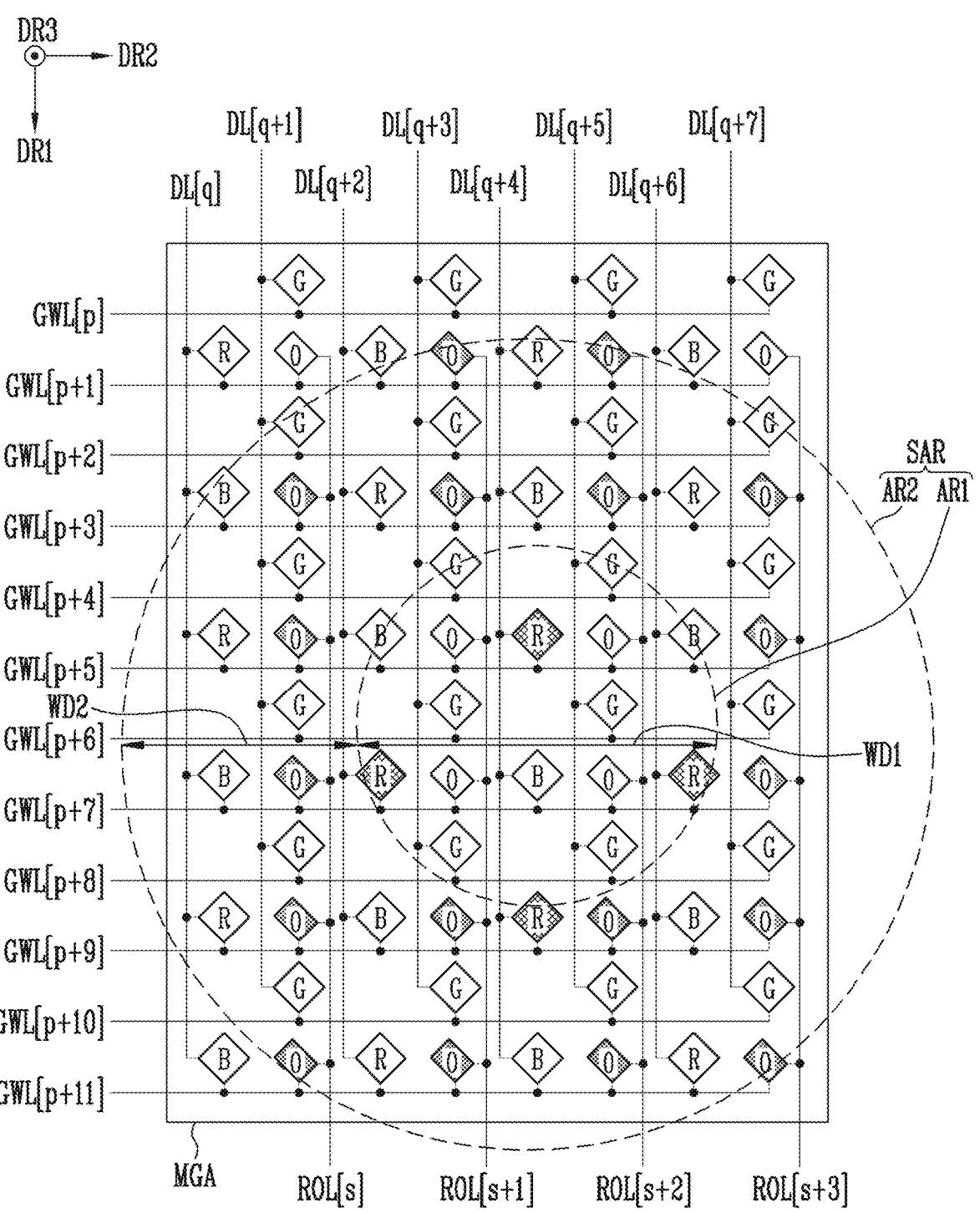

FIGS. 7 and 8 are diagrams illustrating a display device operating in the first mode with respect to the selected area.

Referring to FIG. 7, a scene in which a user's finger UFIG selects a partial area of the display device DD is shown. At this time, the display device DD may operate in the first mode. The first sensing information generated by the readout circuit 60 in the first mode may be photoplethysmography (PPG) information.

The PPG information may be information on a volume of a blood vessel at each time point. When analyzing the information on the volume of the blood vessel, various pieces of information such as a user's pulse wave, oxygen saturation, heart rate, and blood pressure may be obtained.

According to some embodiments, the PPG information may be used to determine whether fingerprint image information is valid (that is, whether the user's finger UFIG is forged or not). That is, the display device DD may determine whether second sensing information is valid using first sensing information. For example, when the blood vessel volume over time does not change, the display device DD may determine that the fingerprint image information is not valid. For another example, when a change pattern of the blood vessel volume over time is different from a pattern of a general human, the display device DD may determine that the fingerprint image information is not valid.

Because the PPG information uses light reflected by blood of a cardiovascular system inside the user's finger UFIG, an area transmitting light and an area receiving reflected light are required to be separated from each other.

Referring to FIG. 8, an area SAR selected by the user's finger UFIG may include a first area AR1 and a second area AR2. In the first mode, a portion of the pixels PX positioned in the first area AR1 of the selected area SAR may emit light in a sensing pattern. The sensing pattern may be a single color pattern. For example, in the first area AR1, only the light emitting elements R of the first color may emit light, and the light emitting elements G and B of the other colors may not emit light. For example, the first color may be red. According to some embodiments, in the first area AR1, only the light emitting elements G of the second color may emit light, and the light emitting elements R and B of the other colors may not emit light. For example, the second color may be green.

The readout circuit 60 may generate the first sensing information using the sensing signals generated by the light sensors FX positioned in the second area AR2, which does not overlap the first area AR1, of the selected area SAR. At this time, the pixels PX positioned in the second area AR2 may be in a non-emission state.

For example, an outer side of the first area AR1 may be completely surrounded by the second area AR2. The are for transmitting light and the area receiving reflected light may be separated from each other by a certain distance. For example, a diameter WD1 of the first area AR1 may be 3 to 4 mm, and a shortest distance WD2 between an outer side and an inner side of the second area AR2 may be 3 to 4 mm. When only area separation is ensured, a shape and a position of the areas AR1 and AR2 may be variously configured. In an example, the first area AR1 and the second area AR2 may be separated, and the first area AR1 may not be surrounded by the second area AR2. In another example, roles of the first area AR1 and the second area AR2 may be replaced with each other. Therefore, a portion of the pixels PX may emit light in the sensing pattern in an inner area and the light sensors FX may receive the reflected light in an outer area. Accordingly, the readout circuit 60 may generate the first sensing information.

Figure 9:
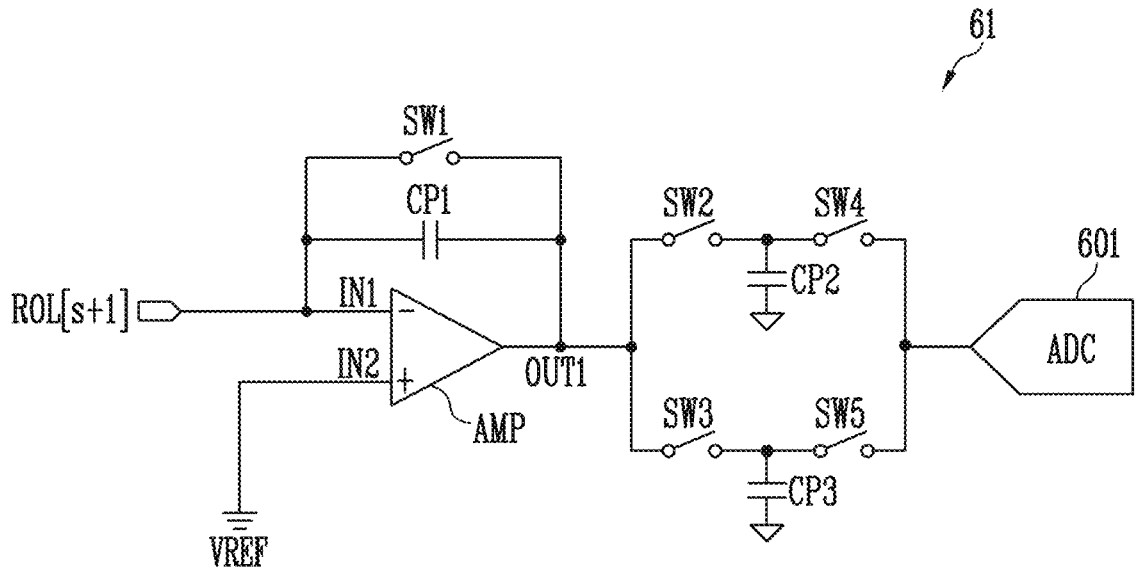
FIG. 9 is a diagram illustrating a readout unit according to some embodiments of the present disclosure.

FIG. 9 is a diagram illustrating a readout unit according to some embodiments of the present disclosure.

The readout circuit 60 may include a plurality of readout units 61. The respective readout units 61 may be connected to corresponding readout lines ROL1 to ROLm.

Referring to FIG. 9, the readout unit 61 according to some embodiments of the present disclosure may include an amplifier AMP, a first capacitor CP1, a first switch SW1, a second switch SW2, a second capacitor CP2, a third capacitor CP3, a fourth switch SW4, a fifth switch SW5, and an analog-to-digital converter 601.

The amplifier AMP may be connected to a portion of the light sensors FX through a readout line ROL[s+1]. For example, a first input terminal IN1 of the amplifier AMP may be connected to the readout line ROL[s+1], and a second input terminal IN2 may receive a reference voltage VREF. The first input terminal IN1 may be an inverting terminal, and the second input terminal IN2 may be a non-inverting terminal. The reference voltage VREF may be a ground voltage. For example, the amplifier AMP may be an operational amplifier (OP Amp).

The first capacitor CP1 may be a configuration for using the amplifier AMP as an integrator. The first capacitor CP1 may be connected between the first input terminal IN1 and an output terminal OUT1 of the amplifier AMP. The first switch SW1 may be connected with the first capacitor CP1 in parallel. The first switch SW1 may be a configuration for initializing a charge stored in the first capacitor CP1 before using an integration function.

The second capacitor CP2 may be a configuration for storing a noise signal. The second switch SW2 may connect the second capacitor CP2 and the output terminal OUT1.

The third capacitor CP3 may be a configuration for storing a sensing signal (or an integrated sensing signal). The third switch SW3 may connect the third capacitor CP3 and the output terminal OUT1.

The analog-to-digital converter 601 may convert analog voltage information stored in the second capacitor CP2 into a digital signal or convert analog voltage information stored in the third capacitor CP3 into a digital signal. For example, the analog-to-digital converter 601 may convert the analog voltage information stored in the second capacitor CP2 into the digital signal when the fourth switch SW4 is turned on. The analog-to-digital converter 601 may convert the analog voltage information stored in the third capacitor CP3 into the digital signal when the fifth switch SW5 is turned on. Turn-on periods of the fourth switch SW4 and the fifth switch SW5 may not overlap each other.

The digital signal generated using the third capacitor CP3 may be sensing information including a noise component. The digital signal generated using the second capacitor CP2 may include only a noise component. Therefore, the display device DD may obtain corrected sensing information by removing the noise component from the sensing information.

Figure 10:
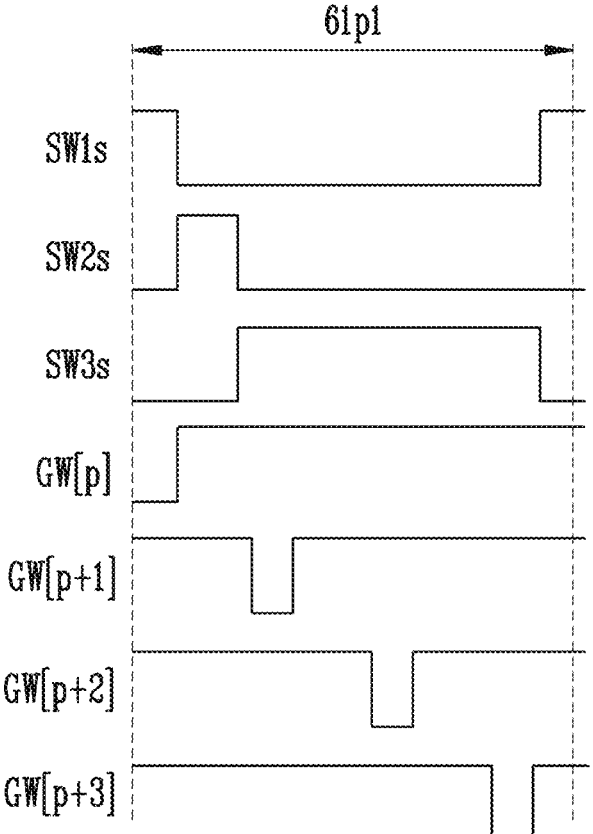
FIGS. 10 and 11 are diagrams illustrating a method of driving the readout unit of FIG. 9 in the first mode according to some embodiments of the present disclosure.
Figure 11:
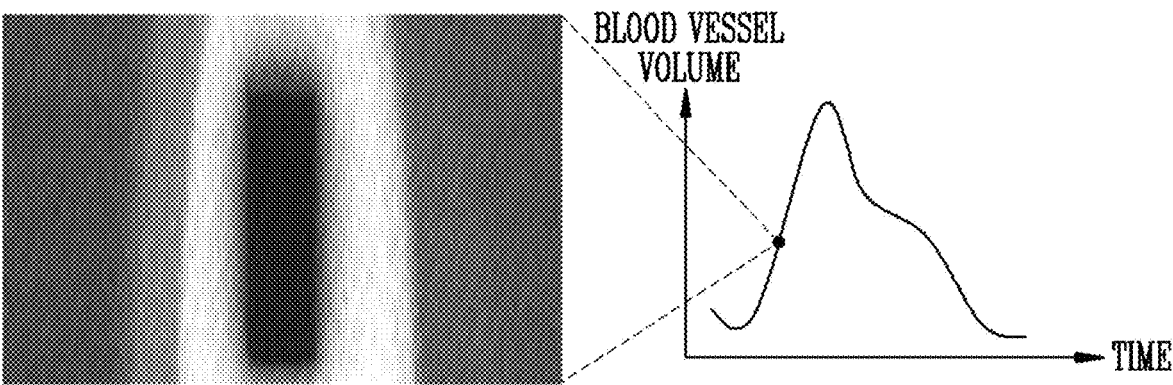

FIGS. 10 and 11 are diagrams illustrating a method of driving the readout unit of FIG. 9 in the first mode.

Referring to FIG. 10, a timing of a first switching signal SW1$s$ for the first switch SW1, a second switching signal SW2$s$ for the second switch SW2, a third switching signal SW3$s$ for the third switch SW3, and first scan signals GW[p], GW[p+1], GW[p+2], and GW[p+3] during one period 61$p$1 of the readout unit 61 in the first mode is shown as an example. It is assumed that the readout unit 61 is connected to the readout line ROL[s+1] (refer to FIG. 8).

First, a first switching signal SW1$s$ of a turn-off level (for example, a low level) may be supplied to the first switch SW1. Accordingly, the first switch SW1 may be in an open state, and the amplifier AMP may operate as an integrator using the first capacitor CP1.

Next, a second switching signal SW2$s$ of a turn-on level (for example, a high level) may be supplied to the second switch SW2. Accordingly, the second switch SW2 may connect the output terminal OUT1 of the amplifier AMP and the second capacitor CP2. At this time, first scan signals GW[p], GW[p+1], GW[p+2], and GW[p+3] of a turn-on level (for example, a low level) overlapping the second switching signal SW2$s$ of the turn-on level do not exist. Therefore, the amplifier AMP1 may store a noise signal other than the sensing signal in the second capacitor CP2.

Next, a third switching signal SW3$s$ of a turn-on level (for example, a high level) may be supplied to the third switch SW3. Accordingly, the third switch SW3 may connect the output terminal OUT1 of the amplifier AMP and the third capacitor CP3. At this time, the third switching signal SW3$s$ of the turn-on level and the first scan signals GW[p+1], GW[p+2], and GW[p+3] of the turn-on level (for example, the low level) may overlap. Referring to FIG. 8, sensing signals generated by the light sensors FX connected to the first scan lines GWL[p+1] and GWL[p+3] and the readout line ROL[s+1] may be stored in the third capacitor CP3. As described above, the sensing signals may include the noise component. The display device DD may obtain corrected first sensing information by removing the previously known noise component from the sensing information.

According to some embodiments, the readout unit 61 may use sensing signals received from two or more light sensors FX during one period 61$p$1 in generation of the first sensing information. Referring to FIG. 11, the PPG information generated during one frame period of the display panel 10 is shown as an image. The PPG information generated during one frame period may be information on the vessel volume at one time point. A resolution of the PPG information is not important, and a light amount received per hour is important. Therefore, according to some embodiments, because the first sensing information is generated using at least two or more light sensors FX during one period 61$p$1 of the readout unit 61, a sufficient light amount may be secured. Therefore, even though the light sensor FX of the same structure is used for PPG sensing and fingerprint image sensing, a sufficient light amount may be secured.

For reference, the light sensor FX used for fingerprint image sensing has a structure that is unfavorable for securing a light amount because a black matrix serving as a diaphragm covers an upper portion. According to some embodiments, because the light sensor FX used for fingerprint image sensing may be used for PPG sensing, a configuration cost may be reduced. In addition, because a separate PPG sensor does not occupy the area of the display panel 10, a high-resolution fingerprint image may be generated using the light sensors FX having a high resolution.

Figure 12:
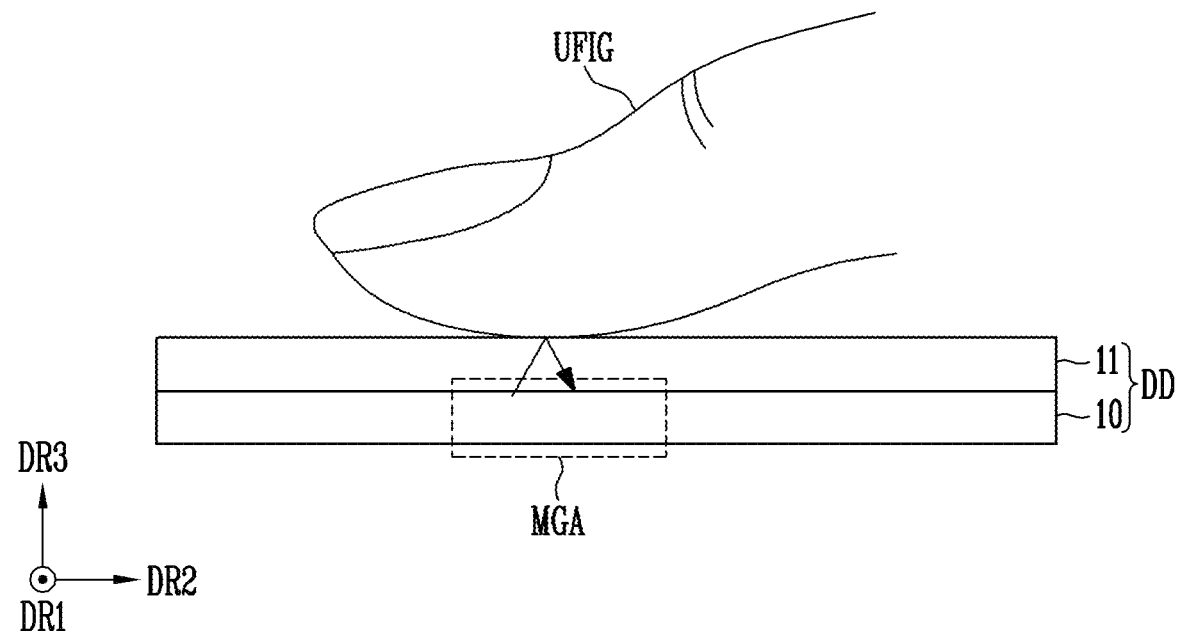
FIGS. 12 and 13 are diagrams illustrating the display device operating in a second mode with respect to the selected area according to some embodiments of the present disclosure.
Figure 13:
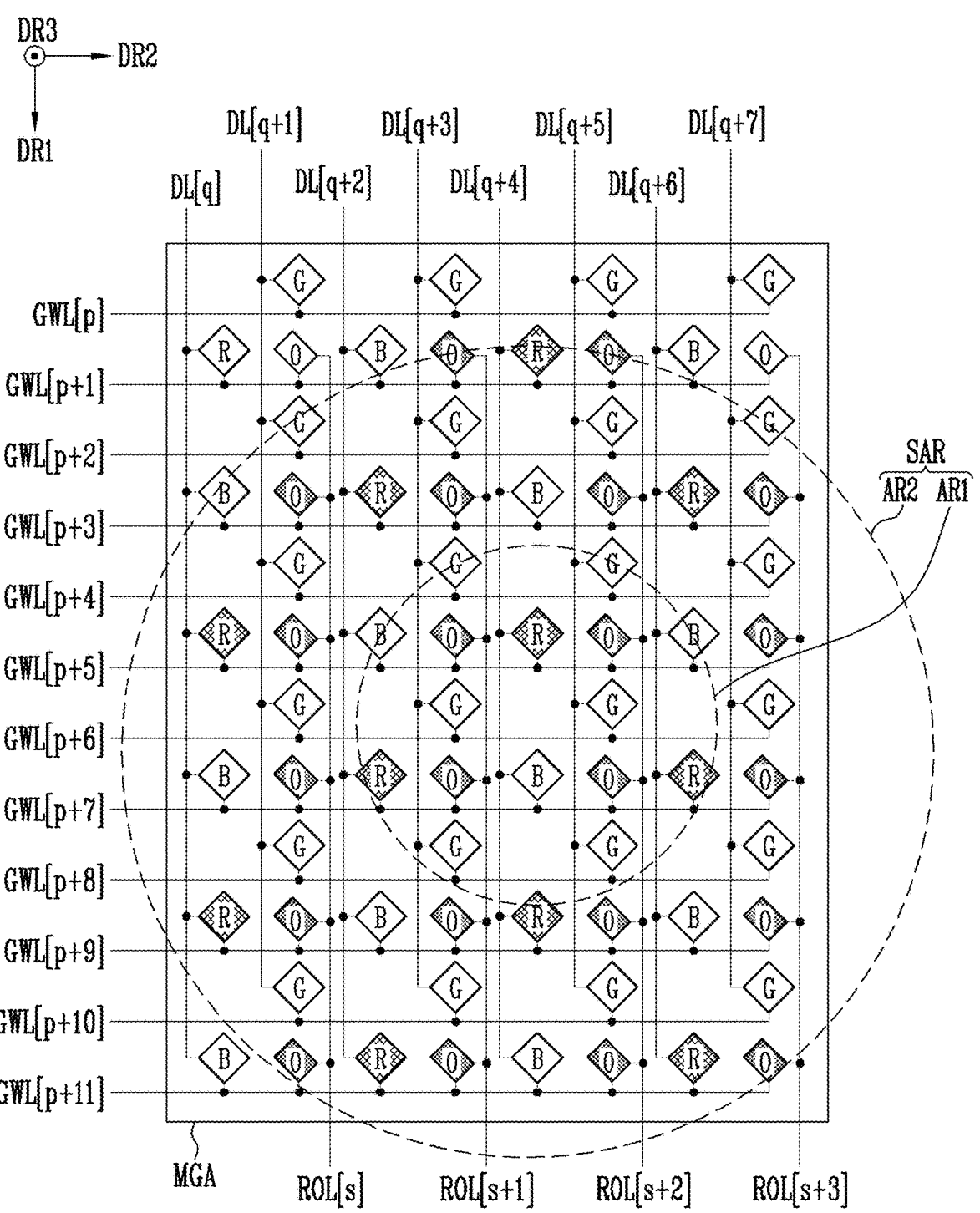

FIGS. 12 and 13 are diagrams illustrating the display device operating in the second mode with respect to the selected area.

Referring to FIG. 12, a scene in which the user's finger UFIG selects a partial area of the display device DD is shown. At this time, the display device DD may operate in the second mode. The second sensing information generated by the readout circuit 60 in the second mode may be the fingerprint image information. Because the fingerprint image information uses light reflected on a surface of the user's finger UFIG, the area transmitting light and the area receiving reflected light may not be distinguished.

Referring to FIG. 13, the area SAR selected by the user's finger UFIG is not required to be separate into the first area AR1 and the second area AR2, differently from FIG. 8. However, in order to compare the first mode and the second mode, embodiments according to the present disclosure are illustrated and described using the first area AR1 and the second area AR2. In the second mode, a portion of the pixels PX positioned in the first area AR1 and a portion of the pixels PX positioned in the second area AR2 may emit light in the sensing pattern. For example, among the pixels PX positioned in the first area AR1 and the second area AR2, only the pixels PX having the light emitting elements R of the first color may emit light. The light emitting elements G and B of the other colors may not emit light. At this time, the sensing pattern may be a single color pattern of the first color. For example, the first color may be red. In another example, among the pixels PX positioned in the first area AR1 and the second area AR2, only the pixels PX having the light emitting elements G of the second color may emit light. The light emitting elements R and B of the other colors may not emit light. At this time, the sensing pattern may be a single color pattern of the second color. For example, the second color may be green.

The readout circuit 60 may generate the second sensing information using the sensing signals generated by the light sensors FX positioned in the first and second areas AR1 and AR2.

Figure 14:
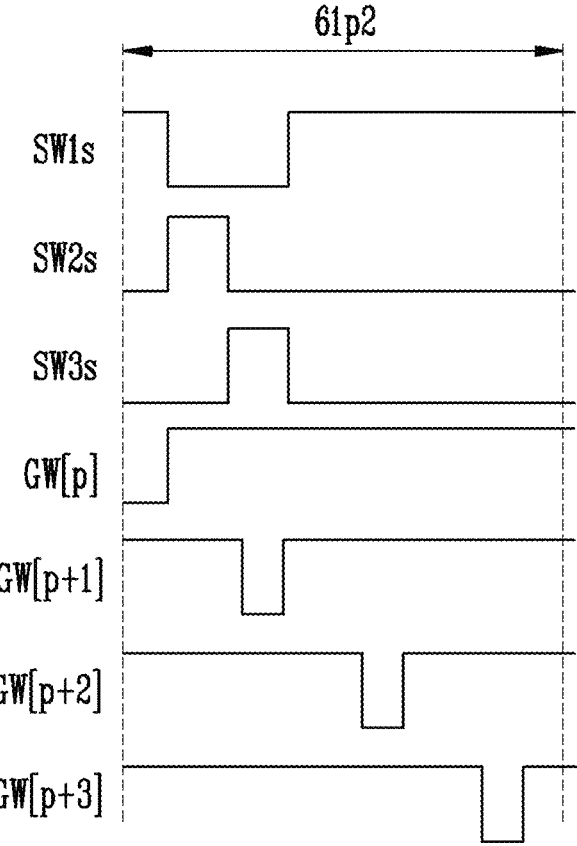
FIGS. 14 and 15 are diagrams illustrating a method of driving the readout unit of FIG. 9 in the second mode according to some embodiments of the present disclosure.
Figure 15:

FIGS. 14 and 15 are diagrams illustrating a method of driving the readout unit of FIG. 9 in the second mode.

Referring to FIG. 14, a timing of the first switching signal SW1*s* for the first switch SW1, the second switching signal SW2*s* for the second switch SW2, the third switching signal SW3*s* for the third switch SW3, and the first scan signals GW[p], GW[p+1], GW[p+2], and GW[p+3] during one period 61*p*2 of the readout unit 61 in the second mode is shown as an example. It is assumed that the readout unit 61 is connected to the readout line ROL[s+1] (refer to FIG. 8). A length of one period 61*p*2 of the readout unit 61 in the second mode may be the same as a length of one period 61*p*1 of the readout unit 61 in the first mode (refer to FIG. 10).

First, a first switching signal SW1*s* of a turn-off level (for example, a low level) may be supplied to the first switch SW1. Accordingly, the first switch SW1 may be in an open state, and the amplifier AMP may operate as an integrator using the first capacitor CP1.

Next, a second switching signal SW2*s* of a turn-on level (for example, a high level) may be supplied to the second switch SW2. Accordingly, the second switch SW2 may connect the output terminal OUT1 of the amplifier AMP and the second capacitor CP2. At this time, first scan signals GW[p], GW[p+1], GW[p+2], and GW[p+3] of a turn-on level (for example, a low level) overlapping the second switching signal SW2*s* of the turn-on level do not exist. Therefore, the amplifier AMP1 may store a noise signal other than the sensing signal in the second capacitor CP2.

Next, a third switching signal SW3*s* of a turn-on level (for example, a high level) may be supplied to the third switch SW3. Accordingly, the third switch SW3 may connect the output terminal OUT1 of the amplifier AMP and the third capacitor CP3. At this time, the third switching signal SW3*s* of the turn-on level and the first scan signal GW[p+1] of the turn-on level (for example, the low level) may overlap. Referring to FIG. 13, a sensing signal generated by the light sensor FX connected to the first scan line GWL[p+1] and the readout line ROL[s+1] may be stored in the third capacitor CP3. As described above, the sensing signal may include the noise component. The display device DD may obtain corrected second sensing information by removing the previously known noise component from the sensing information.

According to some embodiments, the readout unit 61 may use a sensing signal received from one light sensor FX during one period 61*p*2 in generation of the second sensing information. Referring to FIG. 15, the fingerprint image information generated during a plurality of frame periods (for example, 12 frame periods) of the display panel 10 is shown as an image. A resolution of the finger image information is important to accurately authenticate a user. Therefore, according to some embodiments, because the second sensing information is generated using one light sensor FX during one period 61*p*2 of the readout unit 61, a high resolution may be secured. Therefore, even though the light sensor FX of the same structure is used for PPG sensing and fingerprint image sensing, high resolution may be secured.

A generation cycle of the first sensing information may be shorter than a generation cycle of the second sensing information. As described with reference to FIG. 11, the PPG information corresponding to the first sensing information may be generated in one frame period of the display panel DD. Therefore, when only two frame periods or three frame periods of the display panel DD is secured, validity of the PPG of a person may be discriminated. Meanwhile, in order to generate one piece of high resolution fingerprint image information, for example, 12 frame periods may be required. This is because receiving the second sensing information from all light sensors FX included in the selected area SAR during one frame period is difficult (refer to FIGS. 8 and 10).

Hereinafter, with reference to FIGS. 10 and 14, a common point of the readout unit 61 driven in the first mode and the second mode is described. In a state in which the first switch SW1 is turned off, the second switch SW2 and the third switch SW3 may be sequentially turned on. A turn-on period of the second switch SW2 and a turn-on period of the third switch SW3 may not overlap. The turn-on period of the second switch SW2 in the first mode may have the same length as the turn-on period of the second switch SW2 in the second mode.

Hereinafter, with reference to FIGS. 10 and 14, a difference between the readout units 61 driven in the first mode and the second mode is described. A turn-on period of the third switch SW3 in the first mode may be longer than the turn-on period of the third switch SW3 in the second mode. A turn-off period of the first switch SW1 in the first mode may be longer than the turn-off period of the first switch SW1 in the second mode.

Figure 16:
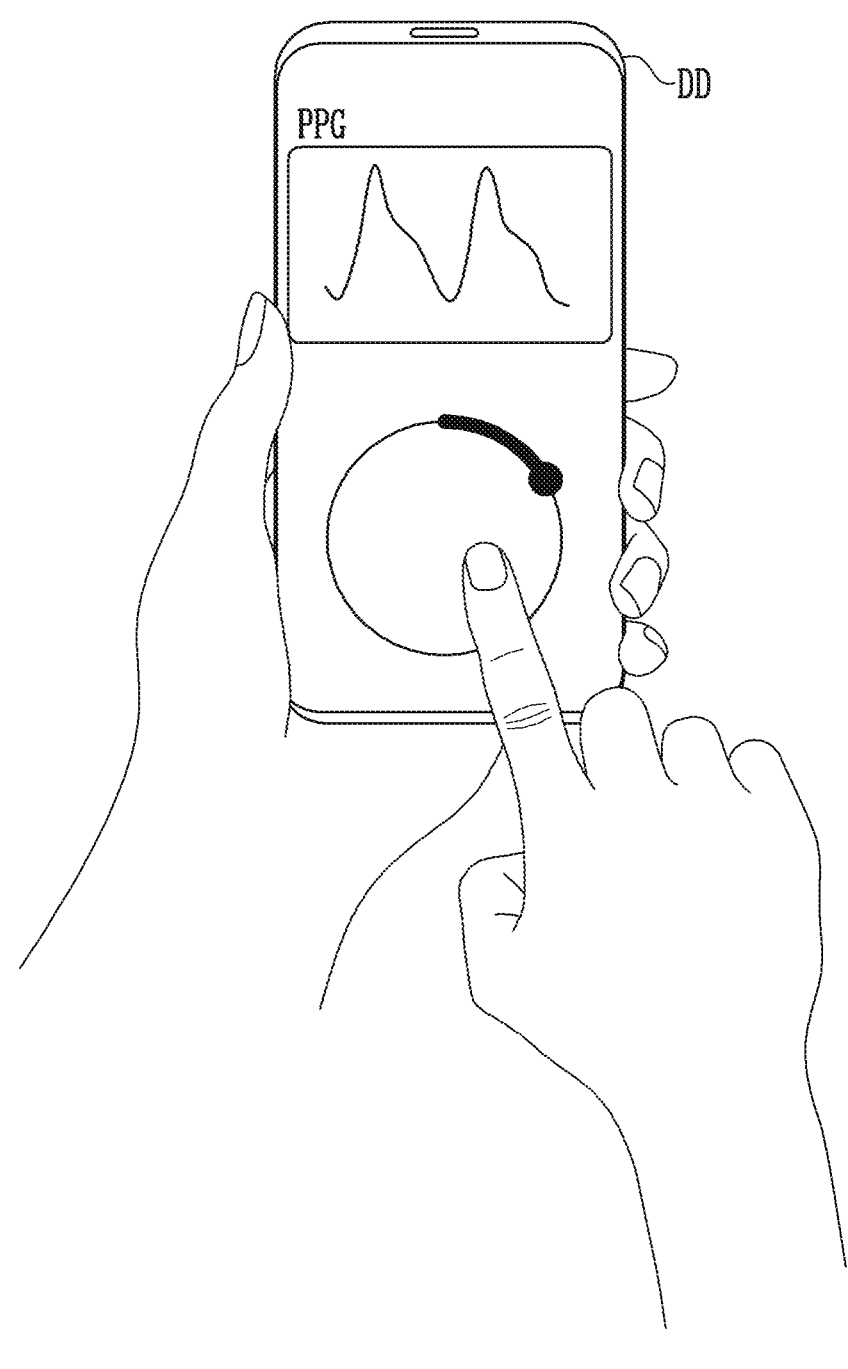
FIGS. 16 and 17 are diagrams illustrating that embodiments of the present disclosure are applied to various display devices.
Figure 17:
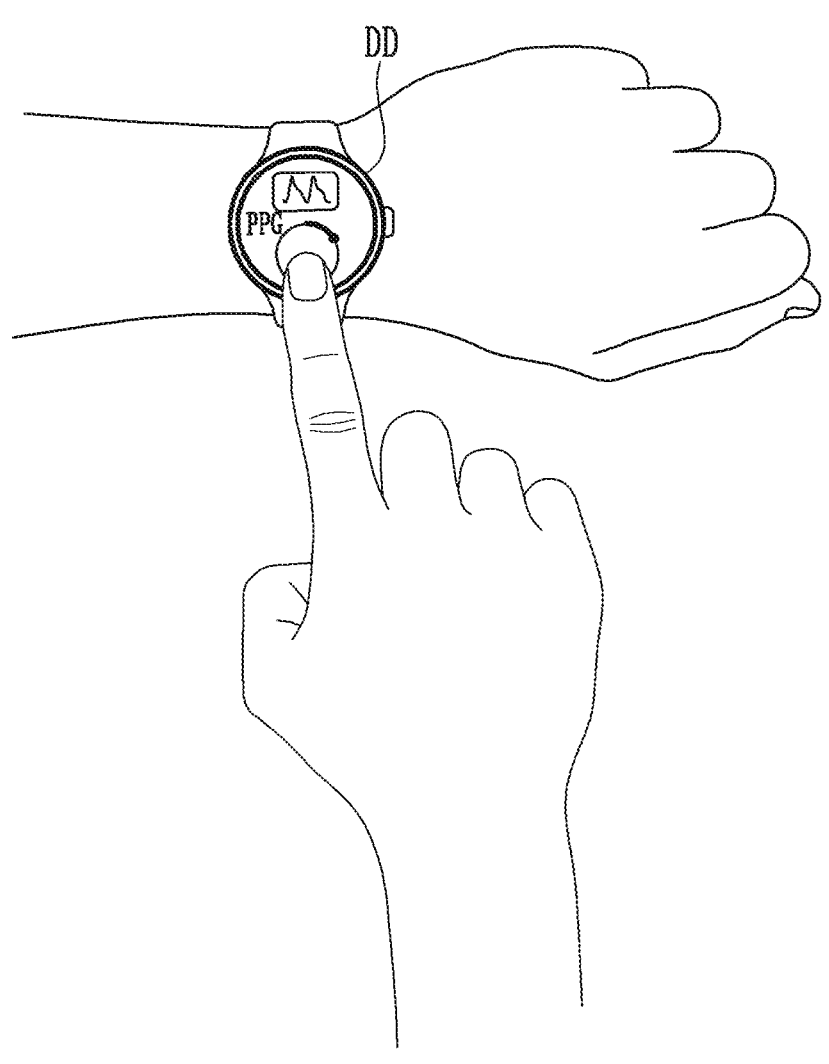

FIGS. 16 and 17 are diagrams illustrating that embodiments of the present disclosure are applied to various display devices.

Referring to FIG. 16, when the display device DD is a mobile display device, a process in which a user performs PPG sensing of the first mode and fingerprint sensing of the second mode with a single touch is shown. The display device DD may first perform the first mode and then perform the second mode during a period in which the user touches. The display device DD may determine whether the second sensing information of the second mode is valid by using the first sensing information of the first mode.

Meanwhile, execution sequences of the first mode and the second mode may be interchanged. For example, the display device DD may first perform the second mode and then perform the first mode during a period in which the user touches. In another example, the display device DD may first perform the first mode, perform the second mode, and finally perform the first mode once more during a period in which the user touches. The execution sequence of the first mode and the second mode may vary according to settings of the display device DD.

The drawings referred to so far and the detailed description of embodiments according to the present disclosure described herein are merely examples of the disclosure, are used for merely describing aspects of some embodiments of the present disclosure, and are not intended to limit the meaning and the scope of embodiments according to the present disclosure as described in the appended claims and their equivalents. Therefore, those skilled in the art will understand that various modifications and equivalent other embodiments are possible from these. Thus, the true scope of embodiments according to the present disclosure should be determined by the technical spirit of the appended claims, and their equivalents.

What is claimed is:

1. A display device comprising:
a plurality of pixels in which at least a first portion of the pixels positioned in a selected area are configured to emit light in a sensing pattern,
a plurality of light sensors configured to generate sensing signals corresponding to a received light amount; and
a readout circuit configured to generate sensing information based on the sensing signals,
wherein the selected area comprises a first area and a second area, and wherein in a first mode, a second portion of pixels positioned in the first area are configured to emit light in the sensing pattern, and the readout circuit is configured to generate first sensing information using sensing signals generated by light sensors positioned in the second area, which does not overlap the first area, and wherein pixels positioned in the second area are in a non-emission state during an entire period of the first mode, wherein the first sensing information is photoplethysmography (PPG) information.

2. The display device according to claim 1, wherein an outer side of the first area is completely surrounded by the second area.

3. The display device according to claim 1, wherein in a second mode, a third portion of the pixels positioned in the first area and a fourth portion of pixels positioned in the second area are configured to emit light in the sensing pattern, and the readout circuit is configured to generate second sensing information using sensing signals generated by light sensors positioned in the first area and the second area.

4. The display device according to claim 3, wherein a generation cycle of the first sensing information is shorter than a generation cycle of the second sensing information.

5. The display device according to claim 3, wherein the second sensing information is fingerprint image information.

6. The display device according to claim 5, wherein whether the second sensing information is valid is determined using the first sensing information.

7. The display device according to claim 3, wherein the readout circuit comprises a readout unit connected to a portion of the light sensors through a readout line, and wherein the readout unit comprises:

an amplifier connected to the portion of the light sensors through the readout line;

a first capacitor connected between a first input terminal and an output terminal of the amplifier;

a first switch connected with the first capacitor in parallel;

a second capacitor;

a second switch connecting the second capacitor and the output terminal;

a third capacitor; and a third switch connecting the third capacitor and the output terminal.

8. The display device according to claim 7, wherein in a state in which the first switch is turned off, the second switch and the third switch are configured to be sequentially turned on.

9. The display device according to claim 8, wherein a turn-on period of the second switch and a turn-on period of the third switch do not overlap.

10. The display device according to claim 8, wherein a turn-on period of the third switch in the first mode is longer than the turn-on period of the third switch in the second mode.

11. The display device according to claim 10, wherein a turn-off period of the first switch in the first mode is longer than a turn-off period of the first switch in the second mode.

12. The display device according to claim 11, wherein a turn-on period of the second switch in the first mode has a same length as a turn-on period of the second switch in the second mode.

13. A method of driving a display device, the method comprising:

selecting a partial area of a plurality of pixels;

emitting light in a sensing pattern by at least a first portion of pixels positioned in a selected area;

generating, by a plurality of light sensors, sensing signals corresponding to a received light amount; and generating, by a readout circuit, sensing information based on the sensing signals, wherein the selected area comprises a first area and a second area, and wherein, in a first mode, a second portion of pixels positioned in the first area emits light in the sensing pattern, and the readout circuit generates first sensing information using sensing signals generated by light sensors positioned in the second area, which does not overlap the first area, and wherein pixels positioned in the second area are in a non-emission state during an entire period of the first mode, wherein the first sensing information is photoplethysmography (PPG) information.

14. The method according to claim 13, wherein an outer side of the first area is completely surrounded by the second area.

15. The method according to claim 13, wherein in a second mode, a third portion of the pixels positioned in the first area and a fourth portion of pixels positioned in the second area emit light in the sensing pattern, and the readout circuit generates second sensing information using sensing signals generated by light sensors positioned in the first area and the second area.

16. The method according to claim 15, wherein a generation cycle of the first sensing information is shorter than a generation cycle of the second sensing information.

17. The method according to claim 15, wherein the second sensing information is fingerprint image information.

18. The method according to claim 17, wherein whether the second sensing information is valid is determined using the first sensing information.

* * * * *